United States Patent [19]
Huber et al.

[11] Patent Number: 5,908,638
[45] Date of Patent: Jun. 1, 1999

[54] PHARMACEUTICAL COMPOSITIONS OF CONJUGATED ESTROGENS AND METHODS FOR THEIR USE

[75] Inventors: Harold Eugene Huber, Cincinnati; Mary Katherine Ryan, Mainville, both of Ohio

[73] Assignee: Duramed Pharmaceuticals, Inc., Cincinnati, Ohio

[21] Appl. No.: 08/690,407

[22] Filed: Jul. 25, 1996

Related U.S. Application Data

[63] Continuation-in-part of application No. 08/507,695, Jul. 26, 1995, abandoned.

[51] Int. Cl.$^6$ .............................. A61K 9/36; A61K 31/56
[52] U.S. Cl. .................. 424/465; 424/464; 424/468; 424/470; 424/472; 424/474; 424/480; 424/482; 514/960
[58] Field of Search ..................... 424/465, 464, 424/469, 480, 484, 488, 495, 474, 475, 481, 482, 468, 470, 472; 514/960, 964, 965

[56] References Cited

U.S. PATENT DOCUMENTS

| | | |
|---|---|---|
| 3,065,143 | 4/1962 | Christenson et al. . |
| 4,369,172 | 12/1981 | Schor et al. . |
| 4,389,393 | 6/1983 | Schor et al. . |
| 4,826,831 | 5/1989 | Plunkett et al. . |
| 5,395,627 | 3/1995 | Dopper et al. . |
| 5,547,948 | 8/1996 | Barcomb ................. 514/170 |
| 5,720,977 | 2/1998 | Deghenghi .............. 424/466 |

FOREIGN PATENT DOCUMENTS

95/17169  6/1995  WIPO .

OTHER PUBLICATIONS

Garraway et al. (1979) Limb Fractures in a Defined Population. I. Frequency and Distribution *Mayo Clin. Proc.* 54: 701–707.

Havlik and Feinleib (1979) Dept. HEW NIH Pub. No. 79–1610.

Conjugated Estrogens, USP23–NF18, 627–628 (1995).

Conjugated Estrogens, USP23–NF18 Supp. 2, 2631–2632 (1995).

*Primary Examiner*—Robert H. Harrison
*Attorney, Agent, or Firm*—Pennie & Edmonds LLP

[57] ABSTRACT

This invention relates to novel pharmaceutical compositions and methods for their preparation containing conjugated estrogens for the treatment of peri-menopausal, menopausal and post-menopausal disorders in women. The novel pharmaceutical compositions comprise a carrier base material and conjugated estrogens formed into a solid unit dosage form possessing a regular incremental release of the medicament upon oral administration. Further, the invention comprises the combination of conjugated estrogens with progestogens in a solid, shaped dosage unit. Specifically, the invention comprises the use of an organic excipient such as high molecular weight hydroxyalkyl alkylcelluloses. The use of an organic excipient such as hydroxypropylmethylcellulose in a stable, solid dosage formulation containing either conjugated estrogens alone or in combination with a progestogen is described.

20 Claims, No Drawings

PHARMACEUTICAL COMPOSITIONS OF CONJUGATED ESTROGENS AND METHODS FOR THEIR USE

CROSS-REFERENCE TO RELATED APPLICATIONS

This application is a continuation-in-part of application Ser. No. 08/507,695 filed Jul. 26, 1995 abnd.

FIELD OF THE INVENTION

This invention relates to novel pharmaceutical compositions comprising a carrier base material combined with a series of compounds known as conjugated estrogens formed into a solid, shaped dosage unit possessing a regular incremental release of the medicament upon oral administration. Further, the invention comprises the combination of conjugated estrogens with progestogens in a solid, shaped dosage unit. Specifically, the invention comprises the use of an organic excipient such as high molecular weight hydroxyalkyl alkylcelluloses. The use of an organic excipient such as hydroxypropylmethylcellulose in a stable, solid dosage formulation containing either conjugated estrogens alone or in combination with a progestogen is described for use in the treatment of menopausal disorders in women.

BACKGROUND OF THE INVENTION

Steroids are used extensively in the treatment of human disease processes. One of the most common classes of steroids are those compounds known as conjugated estrogens. Peri-menopausal, menopausal and post-menopausal women frequently experience a large variety of conditions and disorders related to the decrease of estrogen levels in the body. The decrease in estrogen levels is primarily responsible for hot flashes, vaginal atrophy, osteoporosis (Garraway et al, Mayo Clinic Proceedings, 54, 701–707, (1979)) and the loss of protection against heart attacks in women (Havlik, R. J. and Manning-Feinleid, P. H. 1979, NIH Publication No. 79-1610, U.S. Department of HEW).

It is generally known that estrogen replacement therapy is the most effective method for the treatment of menopausal hot flashes and vaginal atrophy. It is also effective in retarding or preventing osteoporosis. A number of therapeutic regimes for estrogen replacement therapy are known. Plunkett and Wolfe (U.S. Pat. No. 4,826,831) disclose a method of hormonally treating menopausal disorders in women. The administrative regimen comprises the continuous and uninterrupted administration of a progestogen to a woman while cyclically administering an estrogen by using a repetitive dosage regimen. The regimen calls for administering the estrogen continuously for a period of time between about 20 and 120 days, followed by terminating the administration of the estrogen for a period of time between about 3 and 7 days.

The estrogens used in the present disclosure may be those which are orally active and are selected from the group of natural estrogens such as equilin, estrone, 17-α-dihydroequilin, 17-β-dihydroequilin and 17-α-estradiol and their corresponding sulfate esters.

The progestogens useful in this invention are selected from the group comprising medroxyprogesterone acetate, medroxyprogesterone, norethindrone, and progesterone. Other progestogens include, but are not limited to, norethindrone acetate, ethynodiol diacetate, dydrogesterone, norethynodrel, allyl estrenol, lynoestrenol, quingestanol acetate, medrogestone, norgestrienone, dimethisterone, ethisterone, cyproterone acetate, chlormadinone acetate, dl-norgestrel, levo-norgestrel and megestrol acetate.

The present invention provides a novel pharmaceutical composition using low dose estrogens alone or in combination with a progestogen in a continuous uninterrupted fashion where the frequency of administration is at least once daily. The term "continuous" as applied in the specification means that the dosage is administered at least once daily. The term "uninterrupted" means that there is no break in the treatment, and that the treatment is administered at least once daily in perpetuity until the entire treatment is ended.

The carrier base material used in the invention comprises a hydroxyalkyl cellulose and/or a hydroxyalkyl alkylcellulose. The hydroxyalkyl cellulose and/or the hydroxyalkyl alkylcellulose employed in the present invention is exemplified by hydroxyethylcellulose, hydroxypropylcellulose, hydroxybutylethylcellulose, hydroxybutylmethylcellulose, hydroxypropylethylcellulose, hydroxypropylmethylcellulose, hydroxyethylethylcellulose, hydroxyethylmethylcellulose, and mixtures thereof.

Hydroxypropylmethylcelluloses are commercially available in various grades as described by Schor, et al. (U.S. Pat. No. 4,369,172). Commercial designations of the various hydroxypropylmethylculluloses are based on the viscosities of 2% aqueous solutions at 20° C. The viscosities range from 15 cps to 30,000 cps and represent number average molecular weights (Mn) ranging from about 10,000 to over 150,000.

Christenson and Dale (U.S. Pat. No. 3,065,143) disclose the use of certain hydrophilic gums, including hydroxypropylmethylcelluloses, in the preparation of "sustained release" formulations. The tablet disclosed consisted essentially of a drug mixed with a hydrophilic mucilaginous gum which swells when hydrated forming a "soft mucilaginous gel barrier" on the surface of the tablets when brought into contact with the aqueous fluids of the gastrointestinal tract.

The ability to form a mucilaginous gel barrier is dependent upon the molecular weight of the hydrophilic gum. The need to use high molecular weight hydroxypropylmethylcelluloses for this purpose is evident from the specification of U.S. Pat. No. 3,065,143. Other hydrophilic gums having high molecular weights such as sodium carboxymethylcellulose and carboxypolymethylene are effective hydrophilic gums.

Schor, et al. (U.S. Pat. No. 4,369,172) describes the use of a carrier base material combined with a therapeutically active medicament which is shaped and compressed to a solid unit dosage form having a regular and prolonged release pattern upon administration. The carrier base is comprised of hydroxypropylmethylcellulose or a mixture of hydroxypropylmethylcellulose and up to 30% by weight of the mixture of ethylcellulose and/or up to 30% by weight of the mixture of sodium carboxymethylcellulose. The hydroxypropylmethylcellulose has a hydroxypropoxyl content of 9–12 weight percent and a number average molecular weight of less than 50,000. Notably, the formulations described do not form a soft mucilaginous gel. Also, the moisture content of the carrier consisting of: (1) the hydroxypropylmethylcellulose having a hydroxypropoxyl content of 9–12 weight percent, having (2) a number average molecular weight of below 50,000 and, (3) the medicament and other ingredients, if any, has little or no influence on the sustained release characteristics. Further, the moisture content of the finished dosage form plays a minor role as compared to chemical structure of the carrier on the rate of release of the medicaments. The medicaments disclosed do not include conjugated estrogens. Therefore, the sustained release of medicaments depends on the chemical structure of the carrier and is not dependent on the formulation of a soft mucilaginous gel barrier on the surface of the tablet as disclosed in U.S. Pat. No. 3,065,143 or the moisture content of the tablet.

Schor et al. (U.S. Pat. No. 4,389,393) also describes the use of a carrier base material combined with a therapeutically active medicament which is shaped and compressed to a solid unit dosage form having a regular and prolonged release pattern upon administration. The carrier base is comprised of material being one or more hydroxypropyl methylcelluloses or a mixture of one or more hydroxypropyl methylcelluloses and up to 30% by weight of the mixture of methylcellulose, sodium carboxymethylcellulose and/or other cellulose ethers, and wherein at least one of the hydroxypropyl methylcelluloses has a methoxy content of 16–24 weight %, a hydroxypropoxyl content of 4–32 weight percent and a number average molecular weight of at least 50,000. Notably, the carrier base material constitutes less than about one third of the weight of the solid unit dosage form. Thus, an object of U.S. Pat. No. 4,389,393 is to provide a carrier base which comprises less than about one third of the weight of the solid unit dosage form. Additionally, the moisture content of the finished dosage form has little or no influence on the sustained release characteristics and plays a minor role as compared to the chemical structure of the carrier and its concentration on the rate of release of medicaments. The medicaments disclosed in U.S. Pat. No. 4,389,393 do not include conjugated estrogens.

Dopper et al. (U.S. Pat. No. 5,395,627) discloses a process for the preparation of a granule comprising (a) a carrier comprising a diluent and binder and (b) a film coating the carrier wherein the film comprises desogestrel and a lubricant. The stability of the finished granulate is not dependent on its moisture content. Further, the medicaments disclosed in U.S. Pat. No. 5,395,627 do not include conjugated estrogens.

In sharp contrast to the aforementioned patents, the formulations described herein are dependent on the formation of a soft, mucilaginous gel for optimum controlled release of the conjugated estrogens. Furthermore, the stability of the formulations described herein are dependent upon the moisture content of the finished dosage form.

SUMMARY OF THE INVENTION

The present invention is directed toward the use of high molecular weight hydroxypropylmethylcellulose alone or in combination with other hydrophilic gums in the preparation of sustained release solid pharmaceutical unit dosage forms. The moisture content of the finished tablet is critical to the stability and performance of the conjugated estrogens as well as the formation of a soft mucilaginous gel when the tablet is contacted with the aqueous fluids of the gastrointestinal tract. The carrier base also constitutes more than about one third of the sustained release dosage form by weight.

Typical formulations of conjugated estrogens have consisted essentially of inorganic excipients used to prevent degradation of the conjugated estrogens. It has now been surprisingly found that when the moisture content of the formulations described herein is strictly controlled, excellent stability and uniform release of the conjugated estrogens is achieved. Thus, the presence of inorganic excipients is not necessary to stabilize the tablets containing conjugated estrogens if the moisture content of the tablet is strictly controlled. The objects and advantages of the present invention will be further appreciated in light of the following detailed description.

DETAILED DESCRIPTION OF THE INVENTION

The compounds used in this invention are known as conjugated estrogens. The treatment using conjugated estrogens requires the administration of precise dosages of the conjugated estrogens to afford maximum effect.

However, conjugated estrogens are subject to degradation during manufacture. Therefore, the manufacturing process is very important in maintaining the integrity of the dosage form as well as the target dose level of the conjugated estrogens. Further, the conjugated estrogens cannot undergo degradation during storage or the dosage form may lose potency and become subtherapeutic.

Conjugated estrogens as described in the United States Pharmacopeia (USP23) is a mixture of sodium estrone sulfate and sodium equilin sulfate, derived wholly or in part from equine urine or synthetically from estrone and equilin. The most abundant of the estrogens in the standardized blend are the sulfate esters of estrone (1) and equilin (2). The sodium sulfate esters of compounds (1) and (2) are the active components of the formulations described herein.

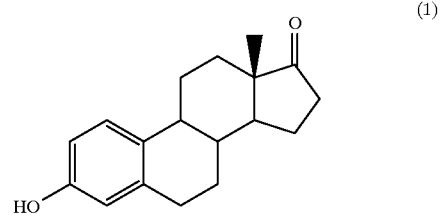

(1)

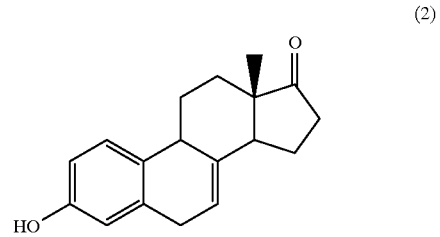

(2)

It contains other conjugated estrogenic substances of the type excreted by pregnant mares.

Concomitant to the sodium sulfate esters of estrone and equilin are the compounds 17-α-dihydroequilin (3), 17-β-dihydroequilin (4) and 17-α-estradiol (5).

Signal impurities derived from degradation of the equilins are 17-α-dihydroequilenin (6), 17-β-dihydroequilenin (7) and equilenin (8).

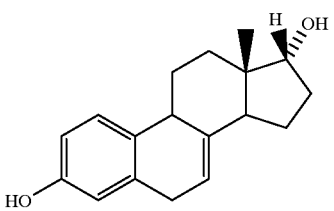
(3)

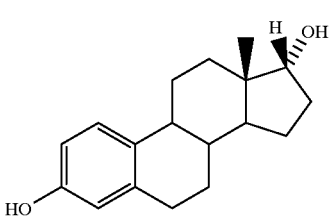
(4)

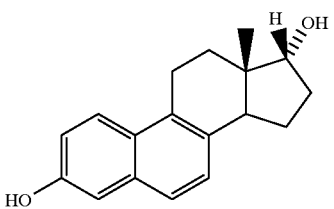
(5)

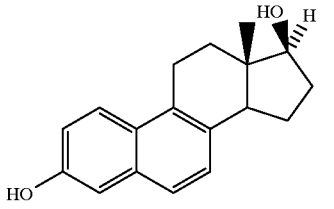
(6)

(7)

(8)

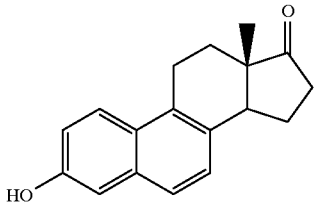

Other sodium sulfate esters of steroids that may be present in conjugated estrogens are 17-β-estradiol (9) and Δ$^{8,9}$-dehydroestrone (10).

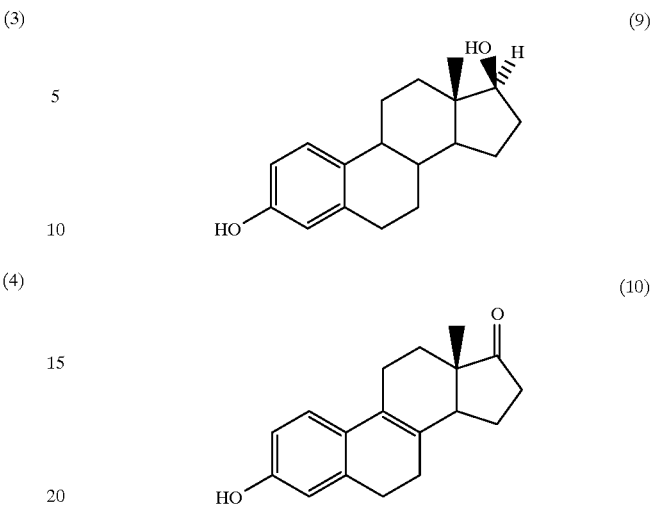
(9)

(10)

Sodium sulfate esters of estrone, equilin and the concomitant components (3), (4) and (5) are required by USP23 to be present in all dosage forms of conjugated estrogens. These compounds are subject to an upper and lower limit of their concentration.

The release of the conjugated estrogens from a dosage form after ingestion by a patient in need thereof must be controlled to prevent rapid absorption from the gastrointestinal tract. If the conjugated estrogens are released immediately, they may produce adverse physiological effects. (*Federal Register*, Vol. 55, No. 30, Feb. 13, 1990, pages 5074–5078). Clinical safety studies on early formulations have been carried out with extended release tablets. (See NDA 20-303).

A variety of mechanisms are employed by one skilled in the art to prevent rapid dissolution of a tableted form of conjugated estrogens. Applying a barrier coating onto the tablet is a typical method used to control the release of orally ingested pharmaceuticals. To obtain an optimally controlled release of the drug substance, the tablet containing the conjugated estrogens must be uniformly coated. This barrier coating can also serve as a moisture barrier which also reduces degradation of the conjugated estrogens during storage by inhibiting the absorption of moisture.

Conjugated estrogens of the type described herein are extremely water sensitive. For example, tablets stored one month at 40° C. with approximately 7% total moisture (4% free water and 3% bound water) exhibited a loss of approximately 3% estrone and 4% equilin. Other tablets stored two months at 40° C. with approximately 8% total moisture (5% free water and 3% bound water) indicated a loss of approximately 7% estrone and 25% equilin. It has now been found that the presence of free water in excess of about 2.5% would cause significant degradation of the conjugated estrogens over a short period of time at ambient temperatures. "Free water" is that water which is not bound covalently or ionically to any of the excipients present in the formulated tablet.

Typically, commercially available conjugated estrogens are purchased as a concentrated powder. (The United States Pharmacopeia 23, National Formulary 18, Official January, 1995). This powder is usually admixed with inert inorganic excipients to be compressed into tablets. The disadvantage in preparing this type of formulation is the potential demixing of the constituents due to differences in particle size and density. The manufacture of tablets containing a uniform dosage thus becomes problematic due to the potential for non-uniformity of the powder.

Another process for making conjugated estrogen tablets involves utilizing a solution which contains dissolved conjugated estrogens. The solution is admixed with inert inorganic excipients to prepare a tablet granulation. This process occurs via adsorption of the liquid containing the conjugated estrogens onto a powdered or solid diluent, particularly an inorganic diluent or excipient via the use of a paddle mixer. The wet granulation is then dried in an oven to remove the solvent. The dried mixture may be further diluted to the desired dose by the addition of other inorganic excipients. The dried mixture is then sized and lubricated to achieve a tablet granulation suitable for compression. This mixture is compressed into tablets, coated with shellac and sugar coated with various colors. Inorganic excipients are used because they contain or retain little or no water which can degrade the conjugated estrogens. The inorganic excipients, which are commonly used for tablet formulation, provide a non-disintegrating tablet base which essentially prolongs the release of the conjugated estrogens from the tablet.

The methods described above for the manufacture of tablets containing conjugated estrogens are suboptimal. The disadvantage to the solution process is the long drying time applied to the wet granulation (4–6 hours). The extended heating period also results in a partial degradation of the conjugated estrogens, particularly the equilins (2), (3) and (4) and generates free steroids. Further, coating of these tablets with shellac can result in tablets with highly variable dissolution rates. The dissolution rate may not only differ between lots, but also within a lot of coated tablets due to the variation in the composition and physical properties of the natural product shellac. Further, the shellac coat tends to polymerize which can also alter the dissolution rate of the tablet over time.

These factors may cause the final dosage form to be unacceptably inconsistent as a result of inconsistent dissolution. Therefore, neither the concentration in plasma nor the activity of the conjugated estrogens would be consistent. This is further aggravated by possible instability during storage due to moisture penetration into the tablet and subsequent degradation of the conjugated estrogens.

As a result of conventional methodologies for manufacturing conjugated estrogen tablets, the patient receives a dosage form which results in inconsistent pharmacokinetics and pharmacodynamics. Therefore, a patient may receive a high or low initial dose from time to time due to the variable bioavailability of the conjugated estrogens.

An object of the invention is to dissolve individual components of the conjugated estrogens in a suitable solvent system. Suitable solvent systems include organic solvents alone such as ethanol and methylene chloride or a combination of a organic solvent and water such as mixtures of ethanol and water. The dissolved estrogens are added to the organic excipients and the mixture is flash dried. The advantages to this method include the minimization of degradation of the conjugated estrogens due to drying the mixture for a shorter period of time compared to conventional methods. Therefore, the content and uniformity of the dosage form is maintained and the quantity and identity of the compounds used in the formulation are not subject to a significant quantitative or qualitative variation from their concentration and composition, respectively, in the original solution containing the conjugated estrogens.

The present invention comprises an orally administered conjugated estrogen tablet formed by adsorbing a conjugated estrogen solution onto a mixture of suitable powders utilizing a fluid bed process. The method of forming the conjugated estrogen tablets of the present invention provides a variety of benefits including controlled release and extended shelf life. The suitable powders include organic excipients such as hydroxypropylmethylcellulose. By employing organic excipients, the release rate of the conjugated estrogens is carefully controlled. After the solution is adsorbed, the mixture is dried to form a steroid composition with less than about 2.5% by weight free water. In the formulations of this invention, the water of hydration typically associated with hydrous organic excipients does not have a detrimental effect on the conjugated estrogens as long as there is less than about 2.5% by weight free water. Additionally, the preparation of the tablet granulation using a minimum amount of free water and heat in a closed system prevents possible contamination of the composition.

This composition is subsequently granulated with a suitable granulating agent such as starch paste. This mixture is then lubricated, compressed into tablets and coated with an organic component which functions as a moisture barrier. Preferably the conjugated estrogen is adsorbed onto the organic excipient using a fluid-bed granulator/dryer.

In order to ensure uniform dissolution of the product, it is preferred that the organic excipient include at least about 30% by weight of an excipient which forms an aqueous gel when contacted with water. This will ensure that each tablet has well controlled dissolution. The preferred moisture barrier coating is comprised primarily of ethylcellulose.

Surprisingly, the organic excipients of the present invention maintain the integrity of the conjugated estrogens as long as the formed tablets are properly coated and contain less than about 2.5% free water. Such organic excipients typically have associated water of hydration with them which can be removed only with difficulty and concomitant degradation of the steroids. For example, 17-α-dihydroequilin sulfate (3) has been found to undergo degradation when an adsorbate containing this material is produced by the standard industry procedure of oven drying. Surprisingly, the water bound to the organic excipients described herein does not cause any deleterious effects to the conjugated estrogens. Further, use of about 30% by weight of an excipient which forms an aqueous gel matrix facilitates uniform diffusion of the conjugated estrogens from the tablet matrix when the moisture protective coating is degraded by the gastrointestinal fluids. When the protective barrier coat is penetrated by the gastrointestinal (G.I.) fluids, water precipitates the formation of a gel matrix as it gradually penetrates through the tablet. Swelling of the tablet further ruptures the barrier coat to permit diffusion of dissolved conjugated estrogens through the gel matrix into the GI tract for subsequent absorption. This provides for a controlled, very uniform dissolution of conjugated estrogens from the tablet and, therefore, uniform dosing of the individual.

According to the present invention, conjugated estrogens are sprayed onto organic excipients and formed into tablets which are then coated with a protective film coating. The organic excipients include hydroxypropylmethylcellulose alone or in combination with other hydrophilic gums such as sodium carboxymethylcellulose, sodium carboxypolymethylene, hydroxypropylcellulose and other cellulose derivatives. Other organic excipients that may be used are carbomer, acacia, gelatin, polyvinyl pyrrolidone, polyethylene glycol and pregelatinized starch.

The conjugated estrogens of the present invention are dissolved in a hydroalcoholic solution. The equilin/estrone ratio has a range from about 0.35 to about 0.65. They are dissolved in a solution of 70% water and 30% ethanol. These steroids can be purchased from, for example, Organic LaGrange of Chicago, Ill. Typical concentrations of the conjugated estrogens are shown in Table 1. The dilute solution of conjugated estrogens is sprayed onto suitable organic excipients which are fluidized at the time of application of the conjugated estrogen solution.

TABLE 1

Conjugated Estrogen Composition

| | *Percent |
|---|---|
| Conjugated Estrogens | |
| Sodium Estrone Sulfate | 52.5–61.5 |
| Sodium Equilin Sulfate | 22.5–30.5 |
| Sum of Sodium Estrone Sulfate and Sodium Equilin Sulfate | 79.5–88.0 |
| Concomitant Conjugated Estrogens | |
| Sodium 17-alpha-Estradiol Sulfate | 2.5–9.5 |
| Sodium 17-alpha-Dihydroequilin Sulfate | 13.5–19.5 |
| Sodium 17-beta-Dihydroequilin Sulfate | 0.5–4.0 |
| Signal Conjugated Estrogens Impurities/Other Substances | |
| Sodium 17-beta-Estradiol Sulfate | NMT 2.25% |
| Sodium 17-alpha-Dihydroequilenin Sulfate | NMT 3.25% |
| Sodium 17-beta-Dihydroequilenin Sulfate | NMT 2.75% |
| Sodium Equilenin Sulfate | NMT 5.50% |
| Sodium $\Delta^{8,9}$ Dehydroestrone Sulfate | NMT 6.25% |

*Percent of estrogens composition calculated as per assay in USP 23, Second Supp., May 15, 1995

There are two types of organic excipients used in the present invention and it is preferable to have a combination of these excipients in order to control release of the drug substances when tablets containing conjugated estrogens are orally ingested. The first type of excipient is a gel-forming excipient which will form a gel in an aqueous solution, excluding the pregelatinized starch binder. Generally about 30–70% by weight, and preferably about 30% of the excipient, will be the gel forming excipient to provide the desired rate of drug substance release. Variation of the amount of the hydroxypropylmethylcellulose will allow the rate of release of conjugated estrogens to be controlled. An increase in the weight percent of hydroxypropylmethylcellulose will slow the release and a decrease in the weight percent of hydroxypropylmethylcellulose will increase the rate of drug substance release.

Suitable organic powder excipients which do not form gels in an aqueous solution (non-gel forming excipients) are the second type of organic excipient used in the present invention. They include lactose, mannitol, cellulose derivatives and other organic materials used for tablet excipients that do not have an adverse pharmacological response when ingested. The gel forming organic excipient and the non-gel forming organic excipient are then combined together, coated with the hydroalcoholic solution of the conjugated estrogens in a fluid-bed granulator/dryer and subsequently granulated with a binder.

A suitable fluid-bed granulator/dryer for use in the present invention is the Glatt® Fluid-bed granulator/dryer which deposits the liquid from a nozzle spraying down onto the fluidized bed of powder which is suspended in air. The operational parameters of the fluid-bed and batch size will be dependent on the fluid-bed product bowl capacity. The hydroalcoholic solution of conjugated estrogens is sprayed until the desired concentration of conjugated estrogens is deposited onto the excipients. Generally, this will be from about 0.3 milligrams to 2.5 milligrams per dosage. By varying the tablet size or the amount of conjugated estrogens liquid sprayed onto the powders, this can be modified. Once the conjugated estrogens have been sprayed onto the organic powders, the organic powders are granulated using a suitable binder, such as pregelatinized starch, gelatin, polyvinyl pyrrolidone (PVP), starch or sodium carboxymethylcellulose.

The resultant granulation is then typically dried in approximately 1 hour in the fluid-bed by increasing the inlet air temperature to a range of about 70 to about 90° C. Using this procedure, no detectable degradation of sodium 17-α-dihydroequilin sulfate (3) is observed with the fluid bed process. It is important that substantially all of the free water be removed during drying. Specifically, the organic powder should have less than about 2.5% free water, which excludes any water of hydration present in the organic excipients. A final granulation moisture content of less than about 2.5%, preferably 2.0% (determined by Loss on Drying) using a moisture analyzer is important for product stability. Therefore, the granulation may be subjected to additional drying in the Glatt® fluid bed if the granulation moisture exceeds 2.0%. After sizing, the granulation is placed in a V-blender and blended. A lubricant such as magnesium stearate is added to the V Blender to lubricate the granules. The lubricated granulation is sampled and tested.

The granulation is then compressed into tablets. Although many types of tablet presses are available, one suitable high-speed press is the Courtoy® Tablet press. This is used to compress the tablets to a strength at which they can withstand the subsequent film coating process. Although tablet hardness will vary depending on tablet size, typically tablets at least 9–10 Strong Cobb Units will satisfactorily withstand the subsequent film coating.

The core tablets must be coated with a moisture barrier film coating which will not dissolve in gastrointestinal fluid over a period of 1–2 hours. This will provide for even release of the estrogens in the tablets. The preferred coating composition is ethylcellulose aqueous dispersion (latex) containing 30–40% solids and a plasticizer such a dibutyl sebacate (DBS) or triethyl citrate. Generally, from 10 to about 40 weight % of the plasticizer will be present. This plasticizer assists in forming an even, flexible coating over the tablet. In addition, 0.5–2.0% of a surfactant may be used such as sodium lauryl sulfate to further facilitate coating.

Other surfactants such as polyoxyethylene (20) sorbitan monopalmitate, polyoxyethylene (20) sorbitan monostearate, polyoxyethylene (20) sorbitan monooleate, polyoxyethylen (20) sorbitan trioleate may be used to facilitate coating of the tablets.

Further, by using ethylcellulose and preparing a dispersion or latex coating, submicron particles of the coating in water are applied to the surface of the tablet and the water is readily evaporated. In contrast, solutions using water-soluble polymers such as hydroxypropylmethylcellulose typically have a slower evaporation rate of the solvent, thus prolonging the tablet's exposure to moisture.

Furthermore, latex films allow for a higher solids content. High solids content allows greater film forming ability, greater barrier protection with minimized exposure to the dispersion medium (water). Upon drying, the polymer particles coalesce forming a continuous film coat.

In addition to ethylcellulose, other barrier coatings that can be used include cellulose acetate phthalate, polyvinyl acetate phthalate, hydroxypropyl methylcellulose phthalate, methacrylic acid copolymer, amylose acetate phthalate, styrene-maleic acid copolymer, cellulose acetate succinate, coacervate gelatin film, cellulose acetate coacervate, polyamide polyvinyl acetate and polyvinylchloride.

Any film coating apparatus can be used to apply the barrier coating. A preferred coating apparatus is an Accela-Cota® Coating pan which utilizes a perforated pan design. The coating is applied at a very slow rate so that the water present in the coating solution can be driven off and not entrapped in the tablet providing a source of free water which could subsequently cause degradation of the conjugated estrogens.

Generally the percent weight gain of the moisture barrier film will be from about 0.5% to about 8% with an approximate coating temperature range of 35–75° C. and an air flow of 900 to 2000 cubic feet per minute (cfm). Once these tablets have been properly dried, they can be stored for a minimum of 2 years without degradation of the conjugated estrogens beyond compendial limits. Further, the film coating remains intact providing for a consistent dissolution rate after ingestion which ensures that the patient repeatedly receives the same dosage in the same manner so that the effects of the estrogens will not vary from dose to dose.

A further object of the invention is a combined hormonal therapy wherein estrogen is administered in combination with progestogens, such as medroxyprogesterone, or androgens, such as testosterone. Accordingly, it is an object of the present invention to provide a tablet which permits such combination therapy.

In applications where combination hormonal therapy is desired, an aqueous or organic solvent suspension of small crystalline particles of finely milled hormonal drug substances may be prepared and coated over the base coated tablet prior to the application of the color coat and final clear coat. Alternatively, the finely milled hormonal drug substance may be admixed and applied with the color coat and then coated with a clear coat. The finely milled hormonal drug substance may also be applied with the clear coat. Suitable organic solvents include all combinations of a lower alcohol and water.

The hormones that would typically be administered in combination with the conjugated estrogen would be progestogens such as progesterone and progesterone derivatives, including medroxyprogesterone, medroxyprogesterone acetate and megestrol acetate. Androgens, such as testosterone and methyl testosterone are also contemplated as a combination with conjugated estrogens.

Several types of polymer base coating suspensions can be used to apply progestogens and androgens. Using this coating technique, the application rate and drying rate can be controlled to provide a uniform distribution of the film coat and good overall appearance. Commonly used polymers include the cellulose ethers, such as hydroxypropylmethylcellulose. A commercially available coating system is Opadry™ (Colorcon Corporation). An Opadry™ color or clear coat may be used to apply the actives to the subcoated tablet. In addition, a pseudolatex system such as Aquacoat™ (ethylcellulose aqueous dispersion, FMC Corporation, Princeton, N.J.) can be used to apply the actives. The ethylcellulose aqueous dispersion can be made water soluble by adding hydroxypropylmethylcellulose as a 1:1 ratio based on solids content and a plasticizer, such as dibutyl sebacate or triethyl citrate.

Equipment to film coat these tablets include the side vented coating pans, such as Accela Cota (Thomas Engineering) or a fluidized-bed bottom spray apparatus, also known as the Wurster apparatus (Glatt Air Techniques, Inc.). Typical solvents for either type of processing equipment include water, isopropanol, ethanol, methanol, acetone, and methylene chloride.

In the Accela Cota coating pan, an active layer of medroxyprogesterone acetate or progesterone can be applied using any one of the coating preparations previously suggested. The active is suspended in the color or clear coating preparation, such as an Opadry™, Opaspray™, or Aquacoat™, and sprayed onto the previously subcoated tablets. The application technique is substantially similar to that used to prepared the subcoat of the tablet. Process parameters such as inlet air temperature, spray rate, exhaust air temperature, and atomization air pressure provide process controls.

The Wurster bottom spray system is also used to coat tablets. The fluidized bed bottom spray method is often used for drug layering, or when applying a large amount of coating material. Advantages for this application of the Wurster spray techniques are good film distribution and uniformity, as well as high coating efficiency.

The design of the Wurster coating chamber creates an organized flow of tablets with the nozzle immersed within the flow pattern and allows an excellent film forming capability. The tablets are in close proximity to the nozzle. The distance the droplet must travel to the tablets is minimal, which minimizes evaporation of the solvent carrier and spreads readily on contact. The tablets are suspended up through the partition into the expansion chamber, and then down onto the outside of the partition. The Wurster apparatus allows uniform thickness and consistency of coating due to the ordered flow pattern of tablets through the coating zone.

For previously subcoated conjugated estrogen tablets, the subcoated tablets provide a robust core that withstands the processing stresses occasioned during tablet manufacture and further serves to minimize surface imperfections in the tablets. Since the nozzle is immersed in the airflow pattern of the tablets, solution evaporation is minimized and the film coat is applied more evenly. The high degree of drying efficiency further makes the Wurster apparatus suitable for coating moisture sensitive drugs such as conjugated estrogen tablets because evaporation of the solvent from the surface of the tablets occurs before any significant penetration into the core of the tablet.

Either conventional Wurster bottom spray system or Glatt's Wurster HS system may be used. In Glatt's HS system the HS collar prevents the tablets from being drawn in too close to the spray nozzle. Therefore, the spray rate can be increased to increase efficiency of the coating. Good reproducible coating efficiency is an important parameter when spraying progestogens such a progesterone and medroxyprogesterone acetate.

The Wurster apparatus is known for a high degree of coating efficiency. However, considerations such as solution concentration, tackiness, and spray rate may affect the process efficiency. Other processing parameters include the fluidization pattern which must be sufficient to keep the tablets aerated in the down bed and the partition height, which controls the suction of the air between the partition and the orifice plate and pulls the tablets horizontally back into the coating zone. Other parameters include the atomizing air and volume, spray rate and inlet air temperature.

The number of partitions will increase with scale up. As many as six or seven partitions may be used in a 46" diameter Wurster. The previously subcoated conjugated estrogen tablets of the present invention provide an excellent core for retaining the supplemental hormonal coating.

The invention may be further defined by the experiments described below.

EXAMPLE 1

A representative tablet of the invention comprises the following ingredients:

| Core Tablet Ingredients | Milligrams/Tablet |
|---|---|
| Lactose | 92.23 |
| Hydroxypropylmethylcellulose | 43.50 |
| Conjugated Estrogens | 0.90 |
| Pregelatinized Starch | 7.65 |
| Magnesium Stearate | 0.73 |
| Film Coating Ingredients | |
| Ethylcellulose Aqueous Dispersion | 1.76 |
| Triethyl Citrate | 0.42 |
| Color Coat | 5.89 |
| Clear Coat | 1.53 |

Tablets manufactured containing the ingredients and amounts shown above coated with ethylcellulose support a 2 year expiration date in the commercial package at 15–30° C. (controlled room temperature).

EXAMPLE 2

A study of the stability of the formulations of the present invention was performed. One of the excipients was lactose hydrous. The total water content was about 5.5% by weight as determined by Karl Fischer titration. The free water was about 2.5% by weight and the water of hydration was about 3% by weight. The amount of conjugated estrogens was 0.625 mg. The amounts of the remaining excipients were substantially the same as in Example 1. Table 2 indicates that tablets packaged for commercial distribution and stored at 25° C. for 12 months showed no degradation of the conjugated estrogens, sodium estrone sulfate and sodium equilin sulfate with total moisture levels between about 4.0–4.8% by weight. Table 3 similarly indicates no degradation where tablets packaged for commercial distribution were stored at 40° C. for six months at 75% relative humidity (RH).

TABLE 2

Conjugated Estrogen 0.625 mg Tablets
Stability of Final Coated Tablet @ Room Temperature (25° C.)

| Station | Total Estrone & Equilin (%) | Estrone % (mg) | Equilin % (mg) | Equilin/Estrone ratio | Karl Fischer Moisture (%) |
|---|---|---|---|---|---|
| Initial | 83.7 | 57.7 (0.361) | 26.0 (0.163) | 0.451 | 4.8 |
| 1 Month | 84.9 | 58.3 (0.365) | 26.5 (0.166) | 0.455 | 4.7 |
| 6 Months | 85.9 | 59.2 (0.370) | 26.7 (0.167) | 0.450 | 4.3 |
| 9 Months | 84.5 | 58.5 (0.366) | 26.0 (0.163) | 0.445 | 4.0 |
| 12 Months | 86.5 | 59.4 (0.371) | 27.1 (0.169) | 0.456 | 4.7 |

TABLE 3

Conjugated Estrogen 0.625 mg Tablets
Stability of Final Coated Tablet @ 40° C. and 75% Relative Humidity

| Station | Total Estrone & Equilin (%) | Estrone % (mg) | Equilin % (mg) | Equilin/Estrone ratio | Karl Fischer Moisture (%) |
|---|---|---|---|---|---|
| Initial | 83.7 | 57.7 (0.361) | 26.0 (0.163) | 0.451 | 4.8 |
| 1 Month | 86.1 | 59.7 (0.373) | 26.4 (0.165) | 0.442 | 4.7 |
| 2 Months | 87.2 | 60.1 (0.375) | 27.1 (0.170) | 0.451 | 4.4 |
| 3 Months | 85.2 | 58.6 (0.366) | 26.6 (0.166) | 0.454 | 4.3 |
| 6 Months | 85.2 | 58.9 (0.368) | 26.3 (0.165) | 0.447 | 4.3 |

EXAMPLE 3

A study was performed to evaluate the effect of inorganic excipients on cracking in the tablet coat. Calcium carbonate and tribasic calcium phosphate were selected for evaluation. Film coat cracking is generally associated with internal stress problems where expansion differences exist between the core tablet and the applied film coat. Due to the inherent expansion properties of inorganic excipients, these materials were subsequently assessed.

The formulas A and B (Table 4) were manufactured using various amounts of tribasic calcium phosphate and calcium carbonate. Batch B was comprised of approximately one-third the quantities of the inorganic excipients used in A. Batch C deleted the inorganic excipients entirely. After compression, these batches were film coated and evaluated at various storage conditions for cracking of the film coat. The compositions are shown in Table 4.

TABLE 4

| | A (mg/tab) | B (mg/tab) | C (mg/tab) |
|---|---|---|---|
| Tribasic Calcium Phosphate | 81.4 | 21.3 | — |
| Calcium Carbonate | 32.0 | 8.4 | — |
| Lactose | 10.0 | 62.8 | 92.5 |
| Hydroxypropylmethylcellulose | — | 43.5 | 43.5 |
| Sodium Carboxymethylcellulose | 6.0 | — | — |
| Starch | 8.5 | 7.7 | 7.7 |
| Magnesium Stearate | 1.5 | 0.7 | 0.7 |
| Conjugated Estrogens | 0.625 | 0.625 | 0.625 |
| Barrier Film Coat (% tablet wt. gain) | 7% | 5% | 5% |

The results of this experiment suggest a correlation between film coat cracking and the presence of inorganic excipients. After film coating and packaging, Batch A tablets developed cracks in the film coat within a few days at ambient conditions. Batch B developed cracks in the film coat after storage at 40° C./75% RH for 2 days in an amber glass bottle with metal cap. However, Batch C did not develop any cracks in the film coat after 12 weeks at 40° C./75% RH or at ambient conditions for six months in the same packages as Batch B.

EXAMPLE 4

A combination tablet is made by applying a suspension of medroxyprogesterone acetate to a core tablet with the moisture barrier coat of Example 1. The suspension consists of small crystalline particles of medroxyprogesterone acetate less than 50 microns, preferably with most of the particles being less than 20 microns. The medroxyprogesterone acetate is applied in a quantity of film coating to provide a tablet of Example 1 with, for example, 2.5 mg to 5.0 mg of medroxyprogesterone acetate per dose.

EXAMPLE 5

A combination tablet is made by applying a suspension of progesterone to a core tablet with the moisture barrier coat of Example 1. The suspension consists of small crystalline particles less than 50 microns, and preferably less than 10 microns. The progesterone is applied in a quantity of film coating to provide a tablet of Example 1 with, for example, 100 mg to 200 mg of progesterone per dose.

EXAMPLE 6

A combination tablet containing conjugated estrogens and a progestogen is made by applying an aqueous based suspension of micronized progestogen in a commercially available coating formula such as an Opadry® Clear Coat. The resulting coating preparation contains approximately 10% solids by weight. In this example, the progestogen is applied to the base coated conjugated estrogen tablet prior to application of the color coat and final clear coat.

EXAMPLE 7

A combination tablet containing conjugated estrogens and a progestogen is made by applying an aqueous based suspension of micronized progestogen in a commercially available coating formula such as an Opadry® Color Coat. The resulting coating preparation contains approximately 22% by weight. In this example, the progestogen is applied to the base coated conjugated estrogen tablet with the color coat and prior to application of the final clear coat.

EXAMPLE 8

A combination tablet containing conjugated estrogens and a progestogen is made by applying an aqueous based suspension of micronized progestogen in a commercially available coating formula such as an Opadry® Color Coat. In this example there is also the addition of the surfactant, polysorbate 80, to facilitate drug dispersion in the coating preparation. The resulting coating preparation contains approximately 22% solids by weight. In this example, the progestogen is applied to the base coated conjugated estrogen tablet with the color coat and prior to the application of the final clear coat.

EXAMPLE 9

A combination tablet containing conjugated estrogens and medroxyprogesterone acetate is made by applying an aqueous based suspension of micronized medroxyprogesterone acetate containing an ethylcellulose dispersion, hydroxypropylmethylcellulose, and dibutylsebacate or triethyl citrate as the film coat. The film coat is applied to the subcoated tablets using an Accela Cota or Wurster apparatus.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description. Such modifications are intended to fall within the scope of the appended claims. All publications cited herein are incorporated by reference in their entirety.

We claim:

1. A pharmaceutical composition in a solid, unit dosage form capable of oral administration for the hormonal treatment of peri-menopausal, menopausal and post-menopausal disorders in a woman comprising:

conjugated estrogens coated onto one or more organic excipients forming a powdered conjugated estrogen composition where said composition is substantially free of inorganic excipients and further comprises about 30–70% gel-forming organic excipient and about 30–70% non-gel forming organic excipient by weight and having less than about 2.5% free water by weight and greater than 2.5% total water wherein said solid unit dosage form is coated with a moisture barrier coating comprising ethylcellulose.

2. A pharmaceutical composition of claim 1 in which said organic excipients include a mixture of one or more gel-forming hydroxyalkylalkylcelluloses and a hydroxyalkyl cellulose wherein said organic excipients constitutes more than about one third by weight of the solid unit dosage form.

3. A pharmaceutical composition of claim 2 in which the gel-forming organic excipients are a mixture of one or more hydroxypropylmethylcelluloses and 0–33% of methyl cellulose or other cellulose ether.

4. A pharmaceutical composition of claim 1 wherein said powdered conjugated estrogen composition further includes at least about 40% by weight of a non-gel forming organic excipient.

5. A pharmaceutical composition of claim 4 wherein said non-gel forming organic excipient is selected from the group consisting of lactose, mannitol, and cellulose derivatives.

6. A pharmaceutical composition of claim 1 wherein said conjugated estrogens is selected from the group consisting of the sodium sulfate esters of estrone, equilin, 17-α-dihydroequilin, 17-β-dihydroequilin and 17-α-estradiol.

7. A pharmaceutical composition of claim 1 wherein said moisture barrier coating is 0.5–8.0% of the total weight of said solid unit dosage form.

8. A pharmaceutical composition of claim 1 wherein the solid unit dosage form is a tablet.

9. A pharmaceutical composition of claim 8 further comprising at least one additional hormone deposited on said tablet after the application of said moisture barrier coat.

10. A pharmaceutical composition of claim 9 wherein said hormone is selected from the group consisting of progesterone, medroxyprogesterone, medroxyprogesterone acetate, testosterone, methyltestosterone and combinations thereof.

11. A pharmaceutical composition of claim 9 wherein said hormone is bonded to said tablet by a polymeric film.

12. A pharmaceutical composition of claim 11 wherein said polymeric film is selected from the group consisting of hydroxypropylmethylcellulose and ethylcellulose aqueous dispersion.

13. A pharmaceutical composition of claim 9 further comprising two or more coatings with one outer coating comprising a polymeric film and at least one additional hormone.

14. A pharmaceutical composition of claim 13 wherein said hormone is selected from the group consisting of progesterone, medroxyprogesterone, medroxyprogesterone acetate, testosterone, methyltestosterone, and combinations thereof.

15. A pharmaceutical composition of claim 14 wherein said hormone is micronized.

16. A pharmaceutical composition of claim 13 wherein said polymeric film contains about 10–30% solids by weight.

17. A pharmaceutical composition of claim 16 wherein said polymeric film further comprises a surfactant.

18. A pharmaceutical composition of claim 17 wherein said surfactant is selected from the group consisting of polyoxyethylene (20) sorbitan monolaurate, polyoxyethylene (20) sorbitan monopalmitate, polyoxyethylene (20) sorbitan monostearate, polyoxyethylene (20) sorbitan monooleate, and polyoxyethylene (20) sorbitan trioleate.

19. A pharmaceutical composition of claim 13 wherein said polymeric film further comprises a plasticizer.

20. A pharmaceutical composition of claim 19 wherein said plasticizer is selected from the group consisting of dibutyl sebacate or triethyl citrate.

* * * * *